(12) United States Patent
Nicolaides et al.

(10) Patent No.: US 9,250,251 B2
(45) Date of Patent: Feb. 2, 2016

(54) METHODS FOR DETERMINING MATERNAL HEALTH RISKS

(75) Inventors: Kypros Nicolaides, London (GB); Tarja Ahola, Turku (FI)

(73) Assignee: WALLAC OY, Turku (FI)

(*) Notice: Subject to any disclaimer, the term of this patent is extended or adjusted under 35 U.S.C. 154(b) by 1050 days.

(21) Appl. No.: 13/259,883

(22) PCT Filed: Apr. 23, 2010

(86) PCT No.: PCT/FI2010/050336
§ 371 (c)(1),
(2), (4) Date: Dec. 23, 2011

(87) PCT Pub. No.: WO2010/122231
PCT Pub. Date: Oct. 28, 2010

(65) Prior Publication Data
US 2012/0135427 A1    May 31, 2012

Related U.S. Application Data

(60) Provisional application No. 61/171,955, filed on Apr. 23, 2009.

(51) Int. Cl.
G01N 31/00    (2006.01)
G01N 33/53    (2006.01)
G01N 33/74    (2006.01)

(52) U.S. Cl.
CPC .......... *G01N 33/74* (2013.01); *G01N 2333/475* (2013.01); *G01N 2800/368* (2013.01)

(58) Field of Classification Search
CPC ................. G01N 2333/471; G01N 2800/368; G06F 19/3431; G06Q 50/24
See application file for complete search history.

(56) References Cited

U.S. PATENT DOCUMENTS

2006/0067937 A1    3/2006    Karumanchi et al.

FOREIGN PATENT DOCUMENTS

WO    WO 2008/005814 A2    1/2008
WO    WO 2008/030283 A1    3/2008

OTHER PUBLICATIONS

Bersinger and Baumann (Immuno-analyse et biologie specialisee, 2009, 24, 58-68).*
Plasencia et al. (Ultrasound Obstet. Gynecol., 2007, vol. 30, pp. 742-749).*
Banzola et al., "Performance of a panel of maternal serum markers in predicting preeclampsia at 11-15 weeks' gestation," Prenat. Diagn. (Jul. 26, 2007), vol. 27, pp. 1005-1010.
Bosio et al., "Plasma P-selectin is elevated in the first trimester in women who subsequently develop pre-eclampsia," British Journal of Obstetrics and Gynaecology (Jul. 2001), vol. 108, pp. 709-715.
Crispi et al., "Predictive value of angiogenic factors and uterine artery Doppler for early- versus late-onset pre-eclampsia and intrauterine growth restriction," Ultrasound Obstet. Gynecol. (2008), vol. 31, pp. 303-309.
Extended European Search Report issued Mar. 27, 2013, in European Patent Application No. 10766705.7.
Madazli et al., "Prediction of preeclampsia with maternal mid-trimester placental growth factor, activin A, fibronectin and uterine artery Doppler velocimetry," International Journal of Gynecology and Obstetrics (2005), vol. 89, pp. 251-257.
Poon et al., "First-Trimester Prediction of Hypertensive Disorders in Pregnancy," Hypertension (2009) vol. 53, pp. 812-818.
Akolekar et al., "Maternal Plasma Plasminogen Activator Inhibitor-2 at 11 to 13 Weeks of Gestation in Hypertensive Disorders of Pregnancy", Hypertension in Pregnancy, 2010, 10 pages.
Akolekar et al., "Maternal Serum Activin A at 11-13 Weeks of Gestation in Hypertensive Disorders of Pregnancy", Fetal Diagnosis and Therapy, vol. 25, 2009, pp. 320-327.
Akolekar et al., "Maternal serum placental growth factor at 11+0 to 13+6 weeks of gestation in the prediction of pre-eclampsia", Ultrasound Obstet Gynecol, vol. 32, 2008, pp. 732-739.
Baumann et al., "Serum markers for predicting pre-eclampsia", Molecular Aspects of Medicine, vol. 28, 2007, pp. 227-244.
Bersinger et al., "Pre-eclampsia: increased, unchanged, and decreased serum markers in comparison to healthy third trimester pregnancy. A synopsis", Immuno-analyse et biologie spécialisée, vol. 20, 2005, pp. 353-359.
Bersinger et al., "Serum markers for pre-eclampsia: An update on the analytes to be determined in the first, second, and thrid trimester", Immuno-analyse et biologie spécialisée; vol. 24, 2009, 58-68.
Cuckle et al., "Estimating a woman's risk of having a pregnancy associated with Down's syndrome using her age and serum alpha-fetoprotein level", British Journal of Obstetrics and Gynaecology, vol. 94, May 1987, pp. 387-402.
Davey et al., "The classification and definition of the hypertensive disorders of pregnancy", Am J Obstet Gynecol, vol. 158, No. 4, Apr. 1988, pp. 892-898.
Draper et al., Applied Regression Analysis, Third Edition, Wiley Series in Probability and Statistics, 1998, 736 pages.
Grudzinskas et al., Screening for Down's Syndrome, Cambridge University Press, 1994, 346 pages.

(Continued)

*Primary Examiner* — Lisa Cook
(74) *Attorney, Agent, or Firm* — Birch, Stewart, Kolasch & Birch, LLP

(57) ABSTRACT

The present description relates to a method for determining the risk of a pregnant woman developing a hypertensive disorder, more specifically gestational hyper-tension or late onset preeclampsia. The present description provides methods useful for determining risk that a pregnant individual will develop a hypertensive disorder or condition of pregnancy, such as gestational hypertension, early preeclampsia, late preeclampsia and related disorders. Several useful combinations of biochemical markers and related clinical population studies are described herein. Additionally, it is proposed herein that certain sets of biochemical markers can be used to determine risk of multiple hypertensive disorders in a single screen. The biochemical markers are PlGF, Activin A and optionally P-Selectin.

2 Claims, 2 Drawing Sheets

(56) References Cited

OTHER PUBLICATIONS

International Search Report for PCT/FI2010/050336 dated Jun. 15, 2010.

Nørgaard-Pedersen et al., "Maternal serum markers in screening for Down syndrome", Clinical Genetics, vol. 37, 1990, pp. 35-43.

Palomaki et al., "Maternal serum •—fetoprotein, age, and Down syndrome risk", Am. J. Obstet Gynecol, vol. 156, No. 2, Feb. 1987, pp. 460-463.

Smets et al., "Novel biomakers in preeclampsia", Clinica Chimica Acta, vol. 364, 2006, pp. 22-32.

Spencer et al., "Free beta human chriogonadotropin in Down's syndrome screening: a multicentre study of its role compared wih other biochemical markers", Ann Clin Biochem, vol. 29, 1992, pp. 506-518.

Wrirtten Opinion for PCT/FI2010/050336 dated Jun. 15, 2010.

Yu et al., "An integrated model for the prediction of preeclampsia using maternal factors and uterine artery doppler velocimetry in unselected low-risk women", American Journal of Obstetrics & Gynecology, vol. 193, 2003, 429-36.

* cited by examiner

| Maternal variables | Unaffected (n=202) | Early preeclampsia (n=26) | Late preeclampsia (n=91) | Gestational hypertension (n=85) |
|---|---|---|---|---|
| Maternal age in yrs, median (IQR) | 32.1 (28.7-35.2) | 32.7 (27.4-38.7) | 31.5 (26.4-36.3) | 33.4 (30.1-35.8) |
| Body mass index in Kg/m², median (IQR) | 25.0 (22.8-28.8) | 27.2 (23.7-32.0) | 27.0 (23.8-33.3)* | 26.7 (24.2-31.4)* |
| Racial origin | | | | |
| White, n (%) | 140 (69.3) | 11 (42.3)* | 40 (44.0)‡ | 63 (74.1) |
| Black, n (%) | 42 (20.8) | 11 (42.3)† | 39 (42.9)‡ | 17 (20.0) |
| Indian or Pakistani, n (%) | 13 (6.4) | 2 (7.7) | 7 (7.7) | 0 |
| Chinese or Japanese, n (%) | 2 (1.0) | 0 | 1 (1.1) | 1 (1.2) |
| Mixed, n (%) | 5 (2.5) | 2 (7.7) | 4 (4.4) | 4 (4.7) |
| Parity | | | | |
| Nulliparous, n (%) | 60 (29.7) | 9 (34.6) | 40 (44.0) | 31 (36.5) |
| Miscarriage / termination < 24 weeks, n (%) | 20 (9.9) | 4 (15.4) | 20 (22.0)* | 16 (18.8) |
| Parous – no previous PE, n (%) | 116 (57.4) | 6 (23.1)† | 22 (24.1)‡ | 29 (34.1)† |
| Parous – previous PE, n (%) | 6 (3.0) | 7 (26.9)† | 9 (9.9) | 9 (10.6)* |
| Cigarette smoker, n (%) | 16 (7.9) | 0 | 6 (6.6) | 7 (8.2) |
| Family history of PE | | | | |
| Mother (n, %) | 6 (3.0) | 3 (11.5) | 11 (12.1)* | 8 (9.4) |
| Sister (n, %) | 5 (2.5) | 3 (11.5) | 1 (1.1) | 0 |
| Conception | | | | |
| Spontaneous, n (%) | 195 (96.5) | 23 (88.5) | 87 (95.6) | 82 (96.5) |
| Ovulation induction, n (%) | 5 (2.5) | 2 (7.7) | 3 (3.3) | 0 |
| In-vitro fertilization, n (%) | 2 (1.0) | 1 (3.8) | 1 (1.1) | 3 (3.5) |
| Medical history | | | | |
| None, n (%) | 195 (96.5) | 21 (80.8)* | 86 (94.5) | 82 (96.5) |
| Chronic hypertension, n (%) | 1 (0.5) | 4 (15.4)† | 4 (4.4) | 0 |
| Diabetes mellitus, n (%) | 2 (1.0) | 0 | 0 | 2 (2.4) |
| Anti-phospholipid syndrome / thrombophilia, n (%) | 3 (1.5) | 1 (3.8) | 1 (1.1) | 1 (1.2) |
| Others, n (%) | 1 (0.5) | 0 | 0 | 0 |
| Medication during pregnancy | | | | |
| None, n (%) | 181 (89.6) | 22 (84.6) | 84 (92.3) | 73 (85.9) |
| Anti-hypertensives, n (%) | 0 | 2 (7.7)* | 2 (2.2) | 0 |
| Insulin, n (%) | 2 (1.0) | 0 | 0 | 2 (2.4) |
| Anti-asthmatics, n (%) | 6 (3.0) | 0 | 3 (3.3) | 3 (3.5) |
| Thyroxine, n (%) | 3 (1.5) | 1 (3.8) | 1 (1.1) | 2 (2.4) |
| Aspirin, n (%) | 4 (2.0) | 1 (3.8) | 0 | 3 (3.5) |
| Anti-depressant, n (%) | 2 (1.0) | 0 | 1 (1.1) | 1 (1.2) |
| Anti-epileptic, n (%) | 4 (2.0) | 0 | 0 | 1 (1.2) |

Fig. 1.

| | Control | Early preeclampsia | Late preeclampsia | Gestational hypertension |
|---|---|---|---|---|
| Mean arterial pressure, median (IQR) | | | | |
| MoM | 0.99 (0.95-1.05) | 1.16 (1.08-1.25)$^{\ddagger}$ | 1.08 (1.02-1.13)$^{\ddagger}$ | 1.08 (1.02-1.14)$^{\ddagger}$ |
| mmHg | 83.8 (80.3-89.2) | 98.0 (91.8-106.5) | 93.5 (87.0-98.7) | 94.4 (86.5-98.3) |
| Lowest uterine artery pulsatility index, median (IQR) | | | | |
| MoM | 1.04 (0.84-1.30) | 1.65 (1.31-1.82)$^{\ddagger}$ | 1.26 (0.93-1.55)$^{\dagger}$ | 1.12 (0.87-1.38) |
| Unit | 1.43 (1.14-1.83) | 2.29 (1.87-2.45) | 1.74 (1.26-2.18) | 1.53 (1.19-1.87) |
| Pregnancy associated plasma protein-A, median (IQR) | | | | |
| MoM | 1.03 (0.71-1.45) | 0.62 (0.42-1.11)$^{\dagger}$ | 0.96 (0.63-1.31) | 0.86 (0.62-1.39) |
| mU/L | 2.85 (1.82-4.66) | 2.63 (0.95-3.36) | 2.87 (1.58-4.32) | 2.01 (1.52-3.45) |
| Free ß-Human chorionic gonadotropin, median (IQR) | | | | |
| MoM | 0.93 (0.63-1.36) | 1.33 (0.76-2.06) | 1.03 (0.73-1.56) | 0.96 (0.63-1.38) |
| U/L | 33.3 (22.9-51.6) | 54.4 (28.4-68.9) | 41.0 (26.4-58.4) | 34.1 (21.6-54.8) |
| Placental growth factor, median (IQR) | | | | |
| MoM | 0.96 (0.75-1.30) | 0.59 (0.49-0.78)$^{\ddagger}$ | 0.84 (0.54-1.02)$^{\dagger}$ | 0.92 (0.68-1.17) |
| pg/mL | 34.3 (26.6-50.0) | 23.0 (15.04-33.5) | 30.3 (21.6-37.0) | 29.6 (23.7-42.4) |
| Inhibin-A, median (IQR) | | | | |
| MoM | 0.97 (0.71-1.42) | 1.52 (0.93-2.00)* | 1.21 (0.87-1.61)* | 1.05 (0.80-1.38) |
| pg/mL | 248.0 (175.5-359.3) | 378.8 (243.6-530.0) | 322.3 (220.2-437.0) | 254.3 (199.5-333.7) |
| Tumor necrosis factor receptor-1, median (IQR) | | | | |
| MoM | 1.00 (0.87-1.13) | 1.10 (0.91-1.32) | 1.08 (0.94-1.19) | 1.02 (0.95-1.15) |
| pg/mL | 1174.8 (1011.4-1303.3) | 1293.0 (1.096.2-1457.6) | 1258.3 (1077.1-1400.2) | 1204.3 (1104.7-1408.0) |
| A disintegrin and metallo-protease 12, median (IQR) | | | | |
| MoM | 1.02 (0.82-1.23) | 1.08 (0.76-1.27) | 1.02 (0.80-1.38) | 1.10 (0.77-1.30) |
| pg/mL | 677.5 (508.5-842.5) | 683.0 (497.5-781.0) | 649.0 (457.0-887.0) | 585.0 (437.0-814.5) |
| Matrix metalloproteinase-9, median (IQR) | | | | |
| MoM | 1.00 (0.71-1.43) | 1.18 (0.86-1.70) | 1.19 (0.92-1.53) | 1.10 (0.84-1.42) |
| pg/mL | 450.6 (321.4-643.8) | 530.2 (387.6-768.1) | 535.7 (415.3-688.2) | 495.4 (380.8-641.0) |
| Activin-A, median (IQR) | | | | |
| MoM | 1.02 (0.77-1.28) | 1.10 (0.92-1.62) | 1.29 (0.94-1.70)$^{\ddagger}$ | 1.09 (0.88-1.28) |
| pg/mL | 1.81 (1.41-2.45) | 2.42 (1.80-2.94) | 2.34 (1.82-3.02) | 2.00 (1.49-2.66) |
| Pentraxin-3, median (IQR) | | | | |
| MoM | 0.98 (0.75-1.24) | 1.11 (0.81-1.66) | 0.94 (0.73-1.52) | 1.05 (0.76-1.38) |
| ng/mL | 0.49 (0.38-0.64) | 0.57 (0.42-0.87) | 0.49 (0.37-0.79) | 0.50 (0.39-0.69) |
| P-selectin, median (IQR) | | | | |
| MoM | 1.01 (0.84-1.25) | 1.27 (0.87-1.51) | 1.20 (0.97-1.42)$^{\ddagger}$ | 1.09 (0.97-1.32)* |
| ng/mL | 29.7 (22.9-35.2) | 35.0 (25.1-40.1) | 35.3 (26.9-40.2) | 32.7 (27.1-38.7) |

Fig. 2.

METHODS FOR DETERMINING MATERNAL HEALTH RISKS

CROSS REFERENCE TO RELATED APPLICATIONS

This application is the National Phase of PCT/FI2010/050336 filed on Apr. 23, 2010, which claims priority under 35 U.S.C. §119(e) to U.S. Provisional Application No. 61/171,955 filed on Apr. 23, 2009, all of which are hereby expressly incorporated by reference into the present application.

Hypertensive disorders such as gestational hypertension (GH) and preeclampsia (PE) affect more than 10% of all pregnancies worldwide. Preeclampsia, which affects about 2-8% of pregnancies, is an important cause of maternal and perinatal mortality and morbidity. Biophysical changes related to these disorders have been studied recently, and theories published. According to a theory, PE is thought to be the consequence of impaired trophoblastic invasion of the maternal spiral arteries leading to placental hypoxia and the release of inflammatory factors which cause platelet and endothelial cell activation and damage. It is also believed, that cytokines are involved in fetoplacental development and have been suggested to be the placental factor capable of damaging endothelial cells and contributing to many of the pathophysiologic changes associated with PE.

Even though studies suggest different biophysical and biochemical indicators being related to hypertensive disorders, currently no routine screens have been adopted for early detection of preeclampsia using maternal blood samples. If the development of GH and PE could be detected earlier, better outcomes, including severity reduction and even recovery could be possible in many cases. During the pregnancy, at an early or later stage, a reliable risk assessment method for developing PE is needed to decrease the potential for negative health outcome of the pregnant woman, the baby or both.

The risk estimation presently generally available is based on obstetric history (e.g. previous PE) and maternal characteristics (e.g. ethnicity and maternal weight) and it can identify only about 30% of early-onset PE cases at 5-10% false positive rate (Yu, C., et al., Am J Obstet Gynecol. 2005; 193:429-36). Yu et al. presented increased identification of women who subsequently develop preeclampsia using combination of ultrasound and maternal factors. However, performing ultrasound is dependent on the skills of health-care personnel involved and requires presence of the pregnant woman during medical examination.

Many biological markers present in maternal samples are currently recognized as associated with preeclampsia. Placental growth factor (PlGF) has been suggested for use in assessing the risk of a pregnant woman developing PE. Ultrasound Obstet Gynecol 32:732-739). Although PlGF has received some acceptance as a reliable marker for preeclampsia, it is desirable to have alternative and additional markers characterized by greater specificity and predictive power.

Even though certain single markers have been studied for their ability to predict pregnancy related complications, there still is a need for methods providing an early estimate on the risk for a pregnant individual developing a hypertensive disorder at a later stage of pregnancy.

Further, there is a need for a method for determining the risk based on an analysis of a biological sample, which can be performed in vitro.

Further, there is a need for a method for determining the risk based on an analysis of a biological sample, which can be performed during the first trimester of pregnancy.

Yet, there still is a need for a method for determining the risk of a hypertensive disorder in a pregnant individual, more specifically gestational hypertension or late onset preeclampsia, said method having improved detection rate in a single screen.

Further, there is a need for a screening method to identify from a population for selecting the pregnant individuals having increased risk for developing a hypertensive disorder in a later stage of pregnancy for further monitoring and possibly treatment.

Additionally, there is need for a method for determining a risk estimate based on a single screen, which can provide differentiation between hypertensive disorders, such as gestational hypertension, late onset preeclampsia and early onset preeclampsia.

SUMMARY OF THE INVENTION

The present description provides methods useful for determining risk that a pregnant individual will develop a hypertensive disorder or condition of pregnancy, such as gestational hypertension, early preeclampsia, late preeclampsia and related disorders. Several useful combinations of biochemical markers and related clinical population studies are described herein. Additionally, it is proposed herein that certain sets of biochemical markers can be used to determine risk of multiple hypertensive disorders in a single screen. As is described in Example 1, the combination of PlGF, Activin A and P-selectin is useful for determining risk of late preeclampsia while a subset of these markers, PlGF and Activin A is useful for determining risk of gestational hypertension, and a single marker, PlGF, in combination with biophysical markers is useful for determining risk of early-preeclampsia.

Provided herein is a method for determining the risk of late onset preeclampsia in a pregnant individual, involving determining the levels of biochemical markers including PlGF, Activin A and P-selectin in one or more blood samples from the individual; and determining the risk of late onset preeclampsia using the determined levels of biochemical markers.

Also provided is a method for determining the risk of gestational hypertension in a pregnant individual, involving determining the levels of biochemical markers including PlGF and Activin A, in one or more blood samples from the individual; and determining the risk of gestational hypertension using the determined levels of biochemical markers.

If desired, these methods can also include determining at least one biophysical marker selected from uterine artery pulsatility index (PI) of the individual and mean arterial pressure (MAP) of the individual; and determining the risk using the levels of the biochemical markers and the at least one biophysical marker.

Provided herein is a method for determining the risk of a hypertensive disorder in a pregnant individual, involving determining the levels of biochemical markers including PlGF, Activin A and P-selectin in one or more blood samples from the individual; determining the risk of late onset preeclampsia using the levels of PlGF, Activin A and P-selectin; and determining the risk of gestational hypertension using the levels of Activin A and PlGF.

Further provided herein is a method for determining the risk of a hypertensive disorder in a pregnant individual, involving determining the levels of biochemical markers including PlGF, Activin A and P-selectin in one or more blood samples from the individual; determining at least one biophysical marker including uterine artery pulsatility index (PI) and mean arterial pressure (MAP) of the individual, determining the risk of late onset preeclampsia using the levels of PlGF, Activin A and P-selectin; determining the risk of gestational hypertension using the levels of Activin A and PlGF; and determining the risk of early onset preeclampsia using the levels of PlGF, the PI and the MAP.

Another method provided herein is for determining the risk of a hypertensive disorder in a pregnant individual, involving determining the levels of biochemical markers including PlGF, Activin A, PAPP-A and P-selectin in one or more blood samples from the individual; determining at least one biophysical marker including uterine artery pulsatility index (PI) and mean arterial pressure (MAP) of the individual, determining the risk of late onset preeclampsia using the levels of PlGF, Activin A and P-selectin; determining the risk of gestational hypertension using the levels of Activin A and PlGF; and determining the risk of early onset preeclampsia using the levels of one or both of PlGF and PAPP-A, the PI and the MAP.

In the following text, the method provided herein will be further described with the aid of a detailed description and with reference to example 1.

BRIEF DESCRIPTION OF THE DRAWINGS

FIG. 1 provides table 1 summarizing maternal results from example 1. Comparison between each hypertensive disorder group and controls is presented in said table by Chi square or Fisher exact test for categorical variables and Mann Whitney-U test for continuous variables, both with post-hoc Bonferroni correction (critical statistical significance $p<0.0167$): *$p<0.0167$, †$p<0.001$, ‡$p<0.0001$.

FIG. 2 lists measured results for each marker in the four outcome groups as table 2. Comparison between each hypertensive disorder group and controls in said table is by Mann Whitney-U test, with post-hoc Bonferroni correction (critical statistical significance $p<0.0167$): *$p<0.0167$, †$p<0.001$, ‡$p<0.000$.

DETAILED DESCRIPTION OF THE INVENTION

Sample

The methods for determining the risk of a hypertensive condition in a pregnant individual involve using a biological sample from the pregnant individual. The biological sample can be any body fluid or tissue sample that contains the selected biochemical markers. The choice of biological sample can often depend on the assay formats available in a particular clinical laboratory for testing levels of markers. For example, some assay formats lack sensitivity needed for assaying whole blood, such that a clinical laboratory opts for testing a fraction of blood, such as serum, or using dried blood. Further, samples that have been preserved, such as by freezing or drying (e.g. on blood card format), are suitable for use in the methods described herein. Example 1 describes use of maternal blood in the form of serum. Exemplary biological samples useful for the methods described herein include blood, purified blood products (such as serum, plasma, etc.), urine, amniotic fluid, a chorionic villus biopsy, a placental biopsy and cervicovaginal fluid. Preferable samples comprise blood samples. This means that the method is carried out in vitro, outside the body of the pregnant woman (also referred to herein as the mother, individual, patient or subject).

Typical assay formats for determining the level of polypeptide and other biomarkers in a sample involve use of a control polypeptide, especially when quantitating levels of such polypeptides. Commercially available proteins and other biomarkers can be used as standards in assays measuring the level of biochemical markers. Alternatively, methods for expressing proteins, such as in prokaryotic and eukaryotic systems, and for synthesizing polypeptides are well known. Full length proteins and fragments thereof can be used as standards for quantitative determination of levels of biomarkers in a sample obtained from a pregnant woman.

By "a control sample" is here meant a sample obtained from a subject being at the same trimester or gestational age of pregnancy, and wherein the pregnancy is confirmed to have a specific outcome in respect to preeclampsia. Typically a "control sample" has been confirmed to have not developed preeclampsia (see Examples herein), although use of a control sample confirmed to have developed preeclampsia is possible. The term is here defined to encompass one or more samples, so that a control sample can be a set of samples obtained from a population. The pregnant controls chosen can be matched to the preeclampsia cases by biophysical parameters, such as maternal age, body mass index, ethnicity and gestational age.

Level of Biochemical Markers

By "determining the levels of biochemical markers including PlGF and Activin A in at least one blood sample from the individual" means that a selected biochemical marker is determined by a method specifically assessing the level of the mentioned marker in a sample obtained from the pregnant woman and from a control sample. The level of a biochemical markers present in a sample can be determined using any assay format suitable for measuring proteins in biological samples. A common assay format for this purpose is the immunoassay, including, for example, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); dissociation-enhanced lanthanide fluorescent immunoassay (DELFIA) and chemiluminescence assays (CL).

A difference in the level of the biochemical marker in the sample relative to control sample indicates the risk of a hypertensive disorder in the woman. The difference can be an increase or decrease in the level of the biochemical marker, depending on the particular biomarker tested.

In certain circumstances, biological samples can be collected on more than one occasion from a pregnant woman, for example, when her hypertensive and/or placental condition requires monitoring for development of gestational hypertension or preeclampsia due to a priori risk, presentation of symptoms and/or other factors. The methods for determining risk of gestational hypertension or preeclampsia described herein can also be used for monitoring a pregnant individual who is undergoing a therapy or treatment for a hypertensive and/or placental condition. If desired, testing of biochemical and/or biophysical markers can be carried out in a home setting, such as by using dipstick biochemical test formats and automated blood pressure machines for home use.

By "an increased risk of developing a hypertensive disorder", "an increased risk of developing gestational hypertension" and "an increased risk of developing late onset preeclampsia" is meant that the likelihood of the subject (pregnant woman) for developing a hypertensive disorder, gestational hypertension and preeclampsia respectively, is on a level, which is higher than in a control group of pregnant women not developing said disorders.

Biochemical Markers

Most interesting biochemical markers in the context of determining the risk of hypertensive disorders in pregnant individuals are PlGF, Activin A and P-selectin.

Previously published studies have shown that a lowered level of PlGF indicates the development of preeclampsia.

The abbreviation "PlGF" means placenta growth factor. PlGF was originally cloned from human term placenta cDNA library in 1991. PlGF has been detected also in other tissues such as heart, lung, muscle and adipose tissue. PlGF belongs to the vascular endothelial growth factor (VEGF) family of proteins. It has a moderate sequence similarity of about 50% to VEGF-A. Alternative splicing generates four isoforms differing in size of which PlGF-1 and PlGF-2 are believed to be the major isoforms. PlGF-1 contains 131 amino acids (MW MONOMER 14.7 kDa, dimer 29.4 kDa). PlGF-2 contains PlGF-1 and of 21 amino acid heparin binding site insertion (MW monomer 17.3 kDa, dimer 34.6 kDa). The length of the full length PlGF-2 protein is thus 152 amino acids. PlGF-3 contains PlGF-1 and 72 amino acid insertion near the C-terminus (MW=monomer 22.8 kDa, dimer 45.6 kDa). Hence, the length of the full length PlGF-3 protein is 203 amino acids. PlGF-4 contains PlGF-3 and 21 amino acid heparin binding site insertion (MW=monomer 26.2 kDa, dimer 52.4 kDa). The length of the full length PlGF-4 is thus 224 amino acids. A reference to PlGF in this text without any definition of the isoform, means PlGF-1.

Activin A is a glycoprotein hormone produced by many tissues but in normal pregnancy the main source is the placenta. Several studies have reported that in patients with preeclampsia (PE) there is a 2-9 fold increase in the maternal serum activin A concentration. There is also evidence that increased levels of activin A precede the clinical onset of PE and may be evident from the first-trimester of pregnancy. (Akolekar R., et al., Fetal Diagn Ther 2009; 25:320-327).

P-selectin is an adhesion molecule found in platelets. In inflammatory and thrombogenic conditions the molecule is expressed on the cell membrane and initiates interactions between endothelial cells, leukocytes and platelets. Platelet activation occurs in normal pregnancy, but this is exaggerated in PE which is characterized by platelet aggregation, vasoconstriction and endothelial injury. The factors controlling platelet activation are unknown but cytokines such as tumor necrosis factor α (TNF-α) have been implicated. The serum concentration of P-selectin, a marker for platelet activation, is increased during established PE and there is also evidence that this elevation may be evident from the first-trimester of pregnancy (Akolekar R., et al. (2010); Maternal plasma P-selectin at 11 to 13 weeks of gestation in hypertensive disorders of pregnancy. Hypertens. Pregnancy, in press).

As is described herein, it has now been recognized that measurement of a combination of PlGF and Activin A in a maternal sample can be used to better determine risk of a pregnant woman developing gestational hypertension. Further combining measurement of P-selectin in addition to said two markers provides improved prediction of the risk of a pregnant woman developing late-onset preeclampsia. The screening performance will thus be improved, as reflected by increased detection rates and lower false positive rates, relative to laboratory tests that employ only PlGF detection.

The selective detection of the markers PlGF and Activin A optionally together with another marker P-selectin, can be combined with any other suitable biochemical markers or other indicators used for assessing the risk of developing preeclampsia, hypertension, placental disorders and the like.

Such biochemical markers are for example those selected from PAPP-A, PAI-1, PAI-2, PlGF-2, PlGF-3, PlGF-4, PP13, VEGF165b and ADAM-12.

As an example, such combination would result in a method for determining the risk of a hypertensive disorder in a pregnant individual, comprising: optionally further refined by determining the levels of biochemical markers including PlGF, Activin A, PAPP-A and P-selectin in one or more blood samples from the individual; determining at least one biophysical marker including uterine artery pulsatility index (PI) and mean arterial pressure (MAP) of the individual, determining the risk of late onset preeclampsia using the levels of PlGF, Activin A and P-selectin; determining the risk of gestational hypertension using the levels of Activin A and PlGF; and determining the risk of early onset preeclampsia using the levels of one or both of PlGF and PAPP-A, the PI and the MAP.

As used herein, the term "PAPP-A" means the metzincin metalloproteinase known as Pregnancy-associated plasma protein A and having an amino acid sequence homologous to GenBank accession number AAH78657. As used herein, the term "PP13" means placental protein 13, also known as galectin-13 having an amino acid sequence homologous to GenBank accession number NP_037400. As used herein, the term "PAI-1" means Plasminogen activator inhibitor 1, also known as PAI and Endothelial plasminogen activator inhibitor, and having an amino acid sequence homologous to UniProt accession number P05121. As used herein, the term "PAI-2" means Plasminogen activator inhibitor 2, also known as Placental plasminogen activator inhibitor, Monocyte Arg-serpin and Urokinase inhibitor, and having an amino acid sequence homologous to UniProt accession number P05120. As used herein, the term ADAM-12 means Disintegrin and metalloproteinase domain-containing protein 12, also known as Meltrin-alpha, and having an amino acid sequence homologous to UniProt accession number O43184. As used herein, the term "VEGF165b" means vascular endothelial growth factor splice variant 165b and having an amino acid sequence homologous to UniProt accession number P15692-8.

Biophysical Markers

The methods described herein can involve determining blood pressure of an individual. One or more measures selected from of systolic blood pressure, diastolic blood pressure and mean arterial blood pressure of the pregnant individual can be used.

The selective detection of the biochemical markers PlGF and Activin A, optionally together with P-selectin can be combined also with any suitable biophysical markers for assessing the risk of developing gestational hypertension. Such biochemical markers are for example blood pressure, mean arterial pressure (MAP) and uterine artery pulsatility index (PI). When applying this embodiment, determining the risk of developing a hypertensive disorder is conducted using both the levels of the biochemical markers and the at least one biophysical marker.

Mean arterial pressure (MAP) refers to the average blood pressure over a cardiac cycle and is determined by the cardiac output (CO), systemic vascular resistance (SVR), and central venous pressure (CVP), using established procedures. A health care provider can use any method to measure the blood pressure of the pregnant individual, including, for example, palpation methods, auscultatory methods and oscillometric methods. Automated blood pressure measuring equipment also can be used.

In an embodiment, the methods described herein can involve determining uterine artery pulsatility index (PI). By "uterine artery pulsatility index" is meant an arterial blood-flow velocity waveform index designed to quantify the pulsatility or oscillations of the waveform. The PI has been found particularly useful in clinical cases in which there is diastolic flow reversal, i.e. bidirectional flow. The PI of the pregnant individual can be measured using any known method. For example, uterine artery Doppler ultrasonography can be performed via the transvaginal or transabdominal route. The uterine artery is first identified with the use of color Doppler ultrasonography. Pulsed-wave Doppler ultrasonography can then be used to obtain waveforms. Various indices can then be calculated. For example PI can be calculated as the peak systolic flow minus the end diastolic flow divided by the mean flow. Although not wishing to be bound by theory, there is evidence that preeclampsia is a consequence of failure of trophoblastic invasion of the maternal spiral arteries. Doppler ultrasound allows assessing the blood flow pattern in the maternal uterine arteries and identifying pregnancies with impaired trophoblastic invasion.

Maternal History

As used herein, "maternal history factors" refers to set of maternal characteristics expected to have impact on the biochemical and biophysical marker levels measured. In the field of adverse pregnancy outcome screening, maternal history is generally accepted to comprise at least maternal age, weeks of gestation, racial origin, cigarette smoking during pregnancy, method of conception, medical history, medication, parity, obstetric history and BMI. To improve reliability of risk calculations, these factors can be included into algorithms. Inclusion of maternal history improves the detection rates of screens during pregnancy. To determine the factors usable in algorithms, maternal history is collected from a population from which relation of a biochemical marker and adverse pregnancy outcomes is determined. Collection is typically based on a questionnaire completed by the individual herself, which is preferably reviewed by a health-care professional together with the patient. When assessing the risk for an individual, same characteristics are collected from her and taken into account when performing the risk determination. Characteristics studied in example 1 were maternal age, racial origin, cigarette smoking during pregnancy, method of conception, medical history, medication, parity, obstetric history and family history of PE in the mother. The collected or measured maternal weight and height can be converted into body mass index (BMI) in $Kg/m^2$.

Statistical Analysis

The Example below includes descriptions of statistical analysis of clinical studies relating to use of biomarkers to determine risk of maternal health conditions. The risk that a pregnant individual develops a hypertensive disorder can be determined from biochemical marker levels using statistical analysis based on clinical data collected in a patient population study. There are multiple statistical methods for combining parameters that characterize the pregnant individual, such as levels of biochemical markers, to obtain a risk estimate. The likelihood method (Palomaki and Haddow, Am. J. Obstet. Gynecol. 156, 460-3 (1987)), the linear discriminant function method (Norgarrd-Pedersen et al. Clin. Genet. 37, 35-43 (1990)) and multiple logistic regression analysis are commonly used for this purpose. As such, the methods described herein for determining risk can be based on use of well known statistical methods, in which a cutoff or a MoM is used to determine risk. It is understood that equivalent well-known statistical approaches can be taken to assess risks of medical conditions.

The basic principle of the likelihood method is that the population distributions for a parameter (such as the level of a biochemical marker) are known for the 'unaffected' and 'affected' groups. Thus, for any given parameter (such as level of marker and blood pressure reading), the likelihood of membership of the 'unaffected' and 'affected' groups can be calculated. The likelihood is calculated as the Gaussian height for the parameter based on the population mean and standard deviation. The 'likelihood ratio' is the ratio of the heights calculated using 'unaffected' and 'affected' population parameters, and is an expression of the increased risk of having a disorder, with respect to a prior risk.

A woman's prior odds (which is a statistical expression related to prior risk, as is described herein below) for having a maternal health condition can be calculated, for example, using a formula derived by clinical population studies (Cuckle et al. 1987). These prior odds can be modified using the likelihood ratio to derive the posterior odds that can be used for the preeclampsia or chromosomal abnormality risk estimate. A detailed description of use of the likelihood method for predicting risk that a fetus has a chromosomal abnormality is set forth, for example, in "Screening for Down's Syndrome," ed. J. G. Grudzinskas, T. Chard, M. Chapman and H. Cuckle; Published by Cambridge University Press, 1994). It is also possible to use observed distributions of likelihood ratios for determining risk using the methods described herein (see, for example, Spencer et al. Ann. Clin. Biochem., 29, 506-18 (1992)).

As an example of an approach for determining a risk that a pregnant woman develops a hypertensive disorder, samples can be collected from a population of women known to have had hypertensive disorders. These samples are analyzed to determine the level of each biochemical marker. The determined level of each biochemical marker would typically then be converted to a multiple of the expected normal median (MoM) specific to a pregnancy of the same gestational age, maternal weight, ethnicity, smoking status, method of conception and parity. Well known statistical regression approaches would then be used for risk calculations (see, for example Draper et al. Applied Regression Analysis (3th ed.) Wiley: New York, N.Y., 1998 and Cuckle H S et al., Estimating a woman's risk of having a pregnancy associated with Down's syndrome using her age and serum alphafetoprotein level. Br. J Obstet Gynecol 1987; 94:387-402; and other references above).

Hypertensive Disorders

The hypertensive disorders occurring during pregnancy, as understood herein, are characterized by symptoms detectable when disorder has developed. If arranged in order of increasing severity, the least severe disorder is gestational hypertension. When in addition to gestational hypertension there is detected proteinuria, it is referred to as preeclampsia, which is divided into late and early onset preeclampsia as defined below. Early onset preeclampsia is the most severe of these disorders.

According to guidelines of the International Society for the Study of Hypertension in Pregnancy (Davey et al., Am. J. Obstet Gynecol; 158; 892098, 1988), Gestational hypertension is described as two recordings of diastolic blood pressure of 90 mmHg or higher at least 4 h apart, and severe hypertension as pressure of at least 110 mm Hg or higher at least 4 h apart or one recording of diastolic blood pressure of at least 120 mm Hg.

As used herein, the term "preeclampsia" means a disorder of pregnancy characterized in part by gestational hypertension and proteinuria. For previously normotensive women, PE is typically defined as gestational hypertension with proteinuria, and severe PE is typically defined as severe gestational hypertension with proteinuria. For women with chronic hypertension, superimposed PE is typically defined as the new development of proteinuria. Aspects of PE useful for making a diagnosis of PE can be classified according to guidelines set out by various medical organizations.

Proteinuria is often described as excretion of 300 mg or more in 24 h or two readings of 2+ or higher on dipstick analysis of midstream or catheter urine specimens if no 24 h collection was available. Women are classified as previously normotensive or with chronic hypertension generally before 20 weeks gestation.

Preeclampsia is understood and shall be defined herein to encompass and reside within a spectrum of preeclampsia disorders, including placental insufficiency, intrauterine growth retardation, early miscarriage, preterm birth, intrauterine death and eclampsia. Although not wishing to be bound by theory, it has been proposed that intrauterine growth retardation reflects an adaptation of the pregnant woman's body to cope with the condition of preeclampsia, which allows the fetus to survive. Early miscarriage and preterm birth, on the other hand, can reflect adaptation of the pregnant woman's body to cope with the condition of preeclampsia, which allow the woman to survive. In this context, intrauterine death would be a failure of this adaptation. Thus, the methods described herein for determining risk of preeclampsia include, and can also be used to determine risk of preeclampsia disorders on the preeclampsia spectrum.

Preeclampsia can develop as early as 20 weeks of gestation and is generally considered "early preeclampsia" or "early onset preeclampsia" if the delivery of a baby is done before week 34 because of pre-eclampsia. As used herein, "late preeclampsia" or "late onset preeclampsia" is defined so that delivery of a baby happens at or after week 34. Early preeclampsia is associated with increased morbidity and thus is considered a more severe form of preeclampsia. The methods for determining the risk of hypertensive disorders described herein are particularily useful for screening for "late preeclampsia." For use in the methods for detecting preeclampsia, a sample can be collected within first trimester, within second trimester and within third trimester. Preferably sample is collected within first trimester. Although earlier testing is often a beneficial policy from a public health perspective, it is understood that collection of samples can sometimes be affected by practical considerations such as a woman delaying a visit to her health care provider until relatively later weeks of gestation.

In instances where a pregnant individual is determined to have an increased risk of developing a hypertensive disorder using a method as described herein, the individual can receive therapy or lifestyle advice from a health care provider. Although there is no widely used treatment for preeclampsia, various studies have shown the benefit of therapies such as anti-hypertensive drugs, such as magnesium sulphate, aspirin, diazepam, and phenytoin; and dietary supplements, such as vitamin D, calcium, and selenium.

Timing of the Determination of Biochemical Marker Levels

The determination of the biochemical markers can be carried out during the first trimester or the second trimester of the pregnancy, or during both of the trimesters. However, the ability to detect a high risk of developing a hypertensive disorder within the first 12 weeks of pregnancy provides more time for a health care provider to provide prevention strategies for the pregnant woman. It is often desirable to complete a risk assessment early in pregnancy, to allow time for measures for preventing or retarding the hypertensive disorder to develop in the pregnant woman.

The methods described herein for determining the risk of a pregnant woman developing gestational hypertension can be practised using a sample obtained from the woman during the first trimester of pregnancy. In a specific embodiment, the sample is obtained during first trimester of pregnancy, preferably during weeks 8-13, more preferably during weeks 11-13, of gestational age. In an embodiment, one or more samples can be obtained from the woman at one or more trimesters of pregnancy. According to another embodiment of the present method, the sample is taken during the second trimester of the pregnancy. Typically this means the weeks 14 to 26 of the pregnancy.

Optionally, one sample can be obtained during the first trimester and another in a later stage of pregnancy, preferably during the second or possibly during third trimester of the pregnancy. The ability to detect a high risk of developing a hypertensive disorder within the first trimester of pregnancy provides more time for a health care provider to provide prevention strategies for the pregnant woman. It is often desirable to complete a risk assessment early in pregnancy, to allow time for measures for preventing or retarding the PE condition to develop in the woman.

Computation of Risks

Typically, results obtained from measurement of levels of biochemical markers are processed using algorithms run on a computer. A computer program which when executed on a computer causes the computer to perform a process for determining risk of a hypertensive disorder, such as gestational hypertension in a pregnant woman. The process can involve inputting a measurement of at least two biomarkers obtained by: i) assaying a sample obtained from the pregnant woman, wherein at least said biochemical markers comprise at least PlGF and Activin A; ii) comparing the level of each biomarker in the sample with the level of the same biomarker in a control sample, wherein a differences in levels of biochemical markers in the sample relative to the control sample are indicative of a hypertensive disorder, and iii) determining a quantitative estimate of said risk based on the result of the comparing.

The computer program can further involve use of at least one additional biochemical marker. In specific embodiments, the said additional biochemical marker is P-selectin and difference in level of P-selectin in the sample in relation to the level in control in addition to PlGF and Activin A, contributes to detection of an increased risk for late onset preeclampsia. Optionally the computer program can further involve use of at least one additional biochemical marker selected from the group comprising PAPP-A, PAI-1, PAI-2, PlGF-2, PlGF-3, VEGF165b, PlGF-4, and ADAM-12.

The computer program can involve inputting a measurement of at least one biomarker obtained by determining one or more biophysical markers of the subject; comparing the one or more biophysical markers of the subject with the same biophysical marker in a control subject, wherein an increased or decreased measure of the one or more biophysical marker in the subject relative to the control is indicative of an increased risk of developing a hypertensive disorder, and determining a quantitative estimate of risk of developing a hypertensive disorder based on the result of the compared one of more biochemical marker and the compared one or more biophysical marker. In particular embodiments, the biophysical marker can be selected from blood pressure and uterine artery pulsatility index.

In the computer program, the process can also include determining the quantitative estimate of risk of a hypertensive disorder comprises determining the likelihood of a hypertensive disorder using a multivariate analysis, and wherein the multivariate analysis comprises using levels of the biochemical markers and distribution parameters derived from a set of control reference data. Preferably, the multivariate analysis is a multivariate Gaussian analysis.

Kit for Assessing Risk of a Hypertensive Disorder in a Pregnant Woman

The method described herein can be employed using kits or commercial packages for assessing risk of a hypertensive disorder in a pregnant woman.

According to one embodiment, the method is employed using at least two kits, one for PlGF, and another for activin A. Another embodiment of the method can be employed using three kits, one for each of PlGF, activin A and P-selectin. Each kit contains at least two binding partners binding specifically to the marker (e.g. PlGF) and at least one of the binding partners is detectable.

According to another embodiment, the kit provides i) at least four detectable binding partners, wherein at least two detectable binding partners bind specifically to PlGF and at least two detectable binding partners bind specifically to Activin A. It can further comprise binding partners, which bind specifically to P-selectin. At least one of binding partners for each marker is detectable.

In embodiments, the detectable binding partner is an antibody or antigen-binding fragment thereof.

In a further specific embodiment, a kit can further provide instructions for using the detectable binding partners in the determination. Reagent volumes, incubation times, reaction conditions etc. can be provided in the instructions.

Detection Method

Herein is provided, in one aspect, a method for determining the risk of a pregnant woman developing a hypertensive disorder. The method involves determining the level of at least two biochemical markers in a sample obtained from a pregnant woman, wherein said biochemical markers comprise PlGF and Activin A; and determining the risk of a hypertensive disorder using the determined levels of biochemical markers. Preferably said hypertensive disorder for which the risk is determined, is gestational hypertension.

In another embodiment, the method for determining the risk of a pregnant woman developing hypertensive disorder further comprises determining the level of biochemical marker P-selectin in said blood sample from the individual. When using the determined levels of biochemical markers PlGF, Activin A and P-selectin said hypertensive disorder for which the risk is determined is late onset preeclampsia.

In an embodiment of the method, determining the risk of a pregnant woman developing a hypertensive disorder, further comprises using maternal history factors.

In an additional embodiment, the levels of said biochemical markers are compared to control values of the same biochemical markers, and a difference in the level of at least one biochemical marker in the sample relative to the control value is indicative of increased risk of developing a hypertensive disorder. Preferably said difference in the level of at least one biochemical marker is selected from:
a. the level of PlGF in a sample obtained from a subject is decreased relative to the level of PlGF in the control sample;
b. the level of Activin A in a sample obtained from a subject is increased relative to the level of Activin A in the control sample;
c. the level of P-selectin in a sample obtained from a subject is increased relative to the level of P-selectin in the control sample.

Better detection rate can be achieved, when a difference in the level of at least two biochemical markers, as described above, in the sample relative to the control value is detected and consequently risk of developing a hypertensive disorder is more reliably indicated. According to one embodiment of the method, decreased level of PlGF and increased level of Activin A in a sample obtained from a subject are indicative of increased risk of gestational hypertension in said subject.

In another embodiment a difference in the level of at least three biochemical markers, as described above, in the sample relative to the control value is indicative of increased risk of developing a hypertensive disorder. In such a case, decreased level of PlGF, increased level of Activin A and increased level of P-selectin in a sample obtained from a subject are indicative of increased risk of late onset preeclampsia.

Observations on Samples

In other words, at least one of the following observations, thus differences in levels, are identified: the level of PlGF in a sample obtained from a subject is decreased relative to the level of PlGF in the control sample; the level of Activin A in a sample obtained from a subject is increased relative to the level of Activin A in the control sample and/or the level of P-selectin in a sample obtained from a subject is increased relative to the level of P-selectin in the control sample. In another embodiment of this method, two of said observations are made in a sample obtained from a subject. In other words, two of said differences occur simultaneously in a sample obtained from a subject. In yet another embodiment, three of said observations are made; hence three of said differences occur simultaneously in a sample obtained from a subject.

Observations Related to Gestational Hypertension

According to one embodiment of the method, when assessing the risk of a pregnant woman developing gestational hypertension the following observations are taken into account:
i) the level of PlGF in a sample obtained from a subject is decreased relative to the level of PlGF in the control sample;
ii) the level of Activin A in a sample obtained from a subject is increased relative to the level of Activin A in the control sample These observations are generated into numerical values, which in an algorithm produce an estimate for the risk of a pregnant woman developing gestational hypertension.

Observations Related to Late Onset Preeclampsia

According to another embodiment of the method, when assessing the risk of a pregnant woman developing late onset preeclampsia the following observations are taken into account:
i) the level of PlGF in a sample obtained from a subject is decreased relative to the level of PlGF in the control sample;
ii) the level of Activin A in a sample obtained from a subject is increased relative to the level of Activin A in the control sample;
iii) the level of P-selectin in a sample obtained from a subject is increased relative to the level of P-selectin in the control sample.

These observations are generated into numerical values, which in an algorithm produce an estimate for the risk of a pregnant woman developing late onset preeclampsia.

Necessarily all observations do not provide significant deviation from standard level simultaneously. For example, taking into account two of said observations still produce increased risk value when fed into algorithm. It is understood, that when all observations are made, and are statistically relevant, algorithm produces high risk estimate.

Method a method for determining the risk of a pregnant woman developing a hypertensive disorder provides a detection rate is at least 45%, preferably at least 50% and more preferably at least 52.7% for false positive rate of 5%. When applying false positive rate of 10%, detection rate is at least 65%, preferably at least 70% and more preferably at least 71.4%.

In an embodiment, depending on the algorithm used, the risk calculation can be based on a difference in ratio of Activin A/PlGF in a sample obtained from a subject relative to the control sample is indicative of an increased risk of developing preeclampsia. In another embodiment, a difference in the ratio of PlGF/Activin A in a sample obtained from a subject relative to the control sample is indicative of an increased risk of developing preeclampsia. In another embodiment, a difference in ratio of P-selectin/PlGF in a sample obtained from a subject relative to the control sample is indicative of an increased risk of developing preeclampsia. In another embodiment, a difference in the ratio of PlGF/P-selectin in a sample obtained from a subject relative to the control sample is indicative of an increased risk of developing preeclampsia. In yet another embodiment, a difference in ratio of Activin A/P-selectin in a sample obtained from a subject relative to the control sample is indicative of an increased risk of developing preeclampsia. In another embodiment, a difference in the ratio of P-selectin/Activin A in a sample obtained from a subject relative to the control sample is indicative of an increased risk of developing preeclampsia.

Exemplary Version of a Method

Briefly, an exemplary version of a method as described herein for determining risk of a hypertensive disorder of a pregnant woman can be performed by taking a blood sample from the pregnant woman. The blood can be processed to prepare plasma or serum if desired. Assay for a biochemical marker would be carried out using a standard immunoassay using at least two antibodies (one coated on the microtiter plate, capture Ab, and another labeled with a detectable label, tracer Ab) specific for a biochemical marker, such as PlGF, Activin A or P-selectin. An example is use of an enzyme linked immunosorbent assay (ELISA) in which intensity of color development in a test sample is proportional to the concentration of marker present. Based on this test, the level of the biochemical marker can be calculated. This level can be used in a risk algorithm independently, or in combination with levels of other markers, if desired. To design the risk algorithm, standard logistic regression analysis of a data set adjusted on the assumption of % prevalence of a hypertensive disorder in the population can be used. To determine whether the level of biochemical markers is greater than or less than normal, the normal level of biochemical marker present in a maternal biological sample from a relevant population is determined. The relevant population can be defined based on any characteristics than can affect normal (unaffected) levels of the markers. For determining risk of gestational hypertension or for late onset preeclampsia, the relevant population can be established on the basis of low risk for gestational hypertension, and for late onset preeclampsia respectively. Once the normal marker levels are known, the determined marker levels can be compared and the significance of the difference determined using standard statistical methods. When there is a statistically significant difference between the determined marker level and the normal level, there is a significant risk that the tested individual will develop a hypertensive disorder.

The level of the selected biochemical marker in the sample is compared with the level of the same biochemical marker in a control sample. A difference in the level of biochemical marker in the sample relative to the control sample is indicative of an increased risk of developing gestational hypertension or late onset preeclampsia. By a difference is meant a statistically significant difference in the values. By the presence of "increased or decreased levels" of any of the biochemical markers means that the level of any of the biochemical marker deviates statistically significantly from the level of the same biochemical marker in a control sample being higher or lower than the level in the control sample.

To analyze the measurement results of a single sample in routine screening for a hypertensive disorder, data of a control population is first needed. This data is obtained by measuring the selected biochemical markers from a large number of samples, preferably more than 100 samples per each week of pregnancy. The measured concentrations of the selected biochemical markers are then preferably $\log_{10}$ transformed to make the distribution of the biological variation Gaussian. Subsequently, a median concentration and standard deviation for each selected biochemical marker is determined for each pregnancy week from the control data. Afterwards, the results of any single sample can be compared to the appropriate median concentrations to determine whether the concentrations of the selected biochemical markers differ from their normal values. This comparison can be used as a basis of calculating the patient risk for gestational hypertension or as a basis of making a diagnosis of gestational hypertension or late onset preeclampsia. An example of such data resulting from studies conducted in example 1 is summarised in table 2 in FIG. 2.

Matched case-control studies can also be made to demonstrate the behaviour of biochemical markers such as the PlGF, Activin A or P-selectin. In such studies, a control population that is matched by physiological parameters to the gestational hypertension or late onset preeclampsia case population is used. Such a study is exemplified in Example 1. Slightly different methods can also be used to calculate the results of such study as compared to routine screening.

Combination of PlGF measurement and the present method a method for determining the risk of a pregnant woman developing a hypertensive disorder As one embodiment, of the method for determining the risk of a pregnant woman developing a hypertensive disorder involves measuring the difference in the level of PlGF, which has been earlier been reported to be indicative of early onset preeclampsia and combining the measuring of at least Activin A or both Activin A and P-selectin to said analysis. These combinations provide further refined prediction of the outcome of the pregnancy. In screening, measuring the level of PlGF only reveals all the individuals having increased risk for developing a hypertensive disorder at a later stage of the pregnancy. However, instead of treating all these individuals equally for severe early onset preeclampsia, now with the present method, those showing a risk for a milder condition, thus gestational hypertension or late onset preeclampsia, can be monitored and treated in a manner suitable for said conditions. This has considerable benefits both considering screened populations and health-care decision-making, and also considering individuals; their habits, concern and even anxiety during pregnancy. In population level, cost savings are achieved by adjusting the frequency of visits to midwife or obstetrician relative to predicted severity of possible hypertensive disorder.

EXAMPLE 1

Examination of Maternal Markers in Hypertensive Disorders of Pregnancy

This was a case-control study. Screening for adverse pregnancy outcomes was performed in women attending for routine assessment of risk for chromosomal abnormalities by measurement of fetal nuchal translucency thickness and maternal serum PAPP-A and free β-hCG at $11^{+0}$-$13^{+6}$ weeks of gestation. Maternal characteristics and medical history were recorded, the uterine artery Doppler was measured by transabdominal color Doppler, blood pressure was measured by automated devices, and serum stored at −80° C. for subsequent biochemical analysis. Written informed consent was obtained from the women agreeing to participate in the study, which was approved by King's College Hospital Ethics Committee.

The blood pressure was taken by automated devices (3BTO-A2, Microlife, Taipei, Taiwan) which were calibrated before and at regular intervals during the study. Recordings were made with the women in the seating position and the MAP was measured as previously described. The PI from both uterine arteries was measured by transabdominal ultrasound as previously described and the lower PI of the two was used for analysis. The results of the MAP and uterine artery L-PI were not given to the women or their doctors and did not influence the subsequent management of the pregnancies.

Maternal Serum Biochemistry

Maternal serum PAPP-A was measured using the DELFIA XPRESS analyzer (PerkinElmer Life and Analytical Sciences, Waltham, USA). The variation of the DELFIA XPRESS PAPP-A assay was determined in 20 runs with two replicates using this DELFIA XPRESS system. The calibration curve of the first run was used as a reference curve during the 14-day-period. The intra-assay and inter-assay variations were 1.2% and 2.1%, respectively, at a PAPP-A concentration of 462 mU/L, 1.4% and 2.3% at 2124 mU/L and 1.3% and 2.5% at 5543 mU/L.

Duplicate serum sample of 100 μl was used to measure PlGF concentration by a quantitative enzyme linked immunoassay (ELISA) technique using Quantikine® human PlGF immunoassay (R&D systems Europe Ltd., Abingdon, UK). The assays were performed on an automated ELISA processor (Dade-Behring BEP 2000, Liederbach, Germany). Absorbance readings were taken on a VICTOR3™ plate reader (PerkinElmer Life and Analytical Sciences, Turku, Finland) and PlGF concentrations were determined using MultiCalc software (PerkinElmer Life and Analytical Sciences, Turku, Finland). The lower limit of detection of the assay was 7 pg/mL and the between-batch imprecision was 8.3% at a PlGF concentration of 48 pg/mL, 5.6% at 342 pg/mL and 5.1% at 722 pg/mL. All samples were analyzed in duplicate and those with a coefficient of variation exceeding 15% were reanalyzed.

Maternal serum concentrations of the following biochemical markers were measured in a case-control population of 117 pregnancies that subsequently developed PE, including 26 that required delivery before 34 weeks (early-PE) and 91 with late-PE and 85 with gestational hypertension (GH) and 202 controls from pregnancies that did not develop any complications and resulted in the live birth of phenotypically normal neonates. Biomarkers measured were: Free β-hCG, PAPP-A, placental growth factor (PlGF), Inhibin-A, Activin A, tumor necrosis factor receptor-1 (TNF-R1), a disintegrin and metalloprotease (ADAM12), matrix metalloproteinase-9 (MMP-9), pentraxin-3 (PTX-3), P-selectin.

The selection of the specific samples from each group of hypertensive disorders was simply based on availability. The cases and controls were matched for length of storage of their blood samples and none of the samples were previously thawed and refrozen.

The definitions of PE and GH were those of the International Society for the Study of Hypertension in Pregnancy. In GH the diastolic blood pressure should be 90 mmHg or more on at least two occasions four hours apart developing after 20 weeks of gestation in previously normotensive women in the absence of significant proteinuria and in PE there should be GH with proteinuria of 300 mg or more in 24 hours or two readings of at least ++ on dipstick analysis of midstream or catheter urine specimens if no 24-hour collection is available. In PE superimposed on chronic hypertension significant proteinuria (as defined above) should develop after 20 weeks of gestation in women with known chronic hypertension (history of hypertension before conception or the presence of hypertension at the booking visit before 20 weeks of gestation in the absence of trophoblastic disease).

Statistical Analysis

The measured MAP, uterine artery L-PI, PAPP-A and free β-hCG were converted to multiples of the median (MoM) of the expected normal median corrected for fetal crown-rump length (CRL), maternal age, BMI or weight, smoking, parity, racial origin and method of conception as previously described R-R The measured concentration of each of the biochemical markers was log transformed to make the distribution Gaussian. Multiple regression analysis was then used to determine which of the factors amongst the maternal characteristics and fetal CRL were significant predictors of each biochemical marker in the control group and from the regression model the value in each case and control was expressed as a MoM. Comparison between each hypertensive disorder group and controls was by Chi square or Fisher exact test for categorical variables and Mann Whitney-U test for continuous variables, both with post-hoc Bonferroni correction (critical statistical significance $p<0.0167$). The probabilities for early-PE, late-PE and GH based on maternal risk factors and a combination of maternal risk factors, MAP and uterine artery L-PI were determined as previously described and logarithmically transformed. Backward stepwise regression analysis was used to determine if the log transformed probability and the log transformed MoMs of any of the biochemical markers had significant contribution in predicting early-PE, late-PE and GH. The performance of screening was determined by receiver operating characteristic (ROC) curves.

The statistical software packages SPSS 15.0 (SPSS Inc., Chicago, Ill.) was used for the data analyses.

Multiple regression analysis in the control group demonstrated that for log PlGF significant independent contributions were provided by fetal CRL, maternal weight, cigarette smoking and racial origin: log expected PlGF=1.199+0.009×CRL in mm−0.003×weight in Kg+(0.196 if smoking, 0 if not)+(0.150 if Black, 0 if other racial origins); $R2=0.254$, $p<0.0001$.

Multiple regression analysis in the control group demonstrated that for log Inhibin-A significant independent contributions were provided by maternal weight and racial origin: log expected Inhibin-A=2.608−0.003×weight in Kg+(0.124 if Black, 0 if other racial origins); $R2=0.079$, $p<0.0001$.

Multiple regression analysis in the control group demonstrated that for log TNF-R1 significant independent contributions were provided by maternal weight and racial origin: log expected TNF-R1=2.982+0.001×weight in Kg+(−0.032 if Black, 0 if other racial origins); $R2=0.057$, $p<0.0001$.

Multiple regression analysis in the control group demonstrated that for log ADAM12 significant independent contributions were provided by fetal CRL, maternal weight and cigarette smoking: log expected ADAM12=2.784+0.005×CRL in mm−0.005×weight in Kg+(−0.076 if smoking, 0 if not); $R2=0.247$, $p<0.0001$.

Multiple regression analysis in the control group demonstrated that for log MMP-9 no significant independent contributions were provided by fetal CRL and maternal characteristics.

Multiple regression analysis in the control group demonstrated that for log Activin A significant independent contributions were provided by maternal age, weight and racial origin: log expected Activin A=0.189+0.009×Age in years−0.003×weight in Kg+(0.107 if Black, 0 if other racial origins); $R2=0.134$, $p<0.0001$.

Multiple regression analysis in the control group demonstrated that for log PTX-3 significant independent contribution was provided by cigarette smoking: log expected PTX-3=−0.285+(−0.121 if smoking, 0 if not); $R2=0.020$, $p<0.0001$.

Multiple regression analysis in the control group demonstrated that for log P-selectin significant independent contributions were provided by racial origin and method of conception: log expected P-selectin=1.480+(−0.058 if Black, −0.249 if Chinese or Japanese, 0 if other racial origins)+(−0.191 if conceived with ovulation drug, 0 if not); $R2=0.096$, $p<0.0001$.

Early Preeclampsia

The patient-specific risk for each hypertensive disorder is calculated from the formula: odds/(1+odds), where odds=eY and for the prediction of early-PE Y is derived from backward stepwise regression analysis of log MoMs of all biochemical markers and log transformed probability for early-PE based on maternal risk factors or a combination of maternal risk factors, MAP and uterine artery PI.

Logistic regression analysis demonstrated that in the detection of early-PE there were significant contributions from log PlGF MoM, log Inhibin-A MoM, log TNF-R1 MoM and log probability based on maternal risk factors:

$Y=3.101+2.680×\log$ probability(maternal risk factor)−$6.274×\log$ PlGF MoM+$2.858×\log$ Inhibin-$A$ MoM+$9.699×\log$ TNF-R1 MoM; $R2=0.524$, $p<0.0001$.

Logistic regression analysis demonstrated that in the detection of early-PE there were significant contributions from log PlGF MoM and log probability based on a combination of maternal risk factors, MAP and uterine artery PI:

$Y=2.655+2.550×\log$ probability(maternal risk factor+MAP+uterine artery PI)−$6.035×\log$ PlGF MoM; $R2=0.706$, $p<0.0001$.

The area under the ROC curve (AUROC) of early-PE in screening by maternal risk factors, PlGF, Inhibin-A and TNF-R1 is 0.913 (95% CI 0.868-0.946) and the detection rates are 80.8% (95% CI 60.6-93.4) and 76.9% (95% CI 56.3-91.0) for false positive rates of 10% and 5%, respectively. The AUROC in screening by maternal risk factors, MAP, uterine artery PI and PlGF is 0.962 (95% CI 0.928-0.983) and the detection rate is 92.3% (95% CI 74.8-98.8) for false positive rates of 10% and 5%.

Late Preeclampsia

For the prediction of late-PE Y is derived from backward stepwise regression analysis of log MoMs of all biochemical markers and log transformed probability for late-PE based on maternal risk factors or a combination of maternal risk factors, MAP and uterine artery PI.

Logistic regression analysis demonstrated that in the detection of late-PE there were significant contributions from log PlGF MoM, log MMP-9 MoM, log Activin A MoM, log P-selectin MoM and log probability based on maternal risk factors:

$Y=4.192+3.079×\log$ probability(maternal risk factor)−$3.478×\log$ PlGF MoM+$2.086×\log$ MMP-9 MoM+$3.667×\log$ Activin $A$ MoM+$4.843×\log$ $P$-selectin MoM; $R2=0.499$, $p<0.0001$.

Logistic regression analysis demonstrated that in the detection of late-PE there were significant contributions from log PlGF MoM, log Activin A MoM, log P-selectin MoM and log probability based on a combination of maternal risk factors, MAP and uterine artery PI.

$Y=3.837+2.893×\log$ probability(maternal risk factor+MAP+uterine artery PI)−$3.208×\log$ PlGF MoM+$3.884×\log$ Activin $A$ MoM+$3.798×\log$ $P$-selectin MoM; $R2=0.572$, $p<0.0001$.

The AUROC of late-PE in screening by maternal risk factors, PlGF, MMP-9, Activin A and P-selectin is 0.877 (95% CI 0.833-0.912) and the detection rates are 61.5% (95% CI 50.8-71.6) and 53.8% (95% CI 43.1-64.4) for false positive rates of 10% and 5%, respectively. The AUROC in screening by maternal risk factors, MAP, uterine artery PI, PlGF, Activin A and P-selectin is 0.900 (95% CI 0.859-0.932) and the detection rates are 71.4% (95% CI 61.0-80.4) and 52.7% (95% CI 42.0-63.3) for false positive rates of 10% and 5%, respectively.

Gestational Hypertension

For the prediction of GH Y is derived from backward stepwise regression analysis of log MoMs of all biochemical markers and log transformed probability for GH based on maternal risk factors or a combination of maternal risk factors, MAP and uterine artery PI.

Logistic regression analysis demonstrated that in the detection of GH there were significant contributions from log P-selectin MoM and log probability based on maternal risk factors:

$Y=2.981+2.183×\log$ probability(maternal risk factor)+$2.179×\log$ $P$-selectin MoM; $R2=0.170$, $p<0.0001$.

Logistic regression analysis demonstrated that in the detection of GH there were significant contributions from log PlGF MoM, log Activin A MoM and log probability based on a combination of maternal risk factors, MAP and uterine artery PI.

$Y=3.481+2.511×\log$ probability(maternal risk factor+MAP+uterine artery PI)−$1.572×\log$ PlGF MoM+$2.008×\log$ Activin $A$ MoM; $R2=0.322$, $p<0.0001$.

The AUROC of GH in screening by maternal risk factors and P-selectin is 0.704 (95% CI 0.648-0.756) and the detection rates are 36.5% (95% CI 26.3-47.6) and 31.8% (95% CI 22.1-42.8) for false positive rates of 10% and 5%, respectively. The AUROC in screening by maternal risk factors, MAP, uterine artery PI, PlGF, Activin A and P-selectin is 0.797 (95% CI 0.746-0.842) and the detection rates are 52.9% (95% CI 41.8-63.9) and 38.8% (95% CI 28.4-50.0) for false positive rates of 10% and 5%, respectively.

The invention claimed is:
1. Method for determining the risk of late onset preeclampsia in a pregnant individual, comprising:
   detecting the levels of biochemical markers placental growth factor (PlGF), Activin A and P-selectin in at least one blood sample from the pregnant individual; and
   determining the increased risk of late onset preeclampsia if any of (i) to (iii) occur;

(i) when the level of PlGF in the blood sample obtained from the individual is decreased relative to the level of PlGF in a control sample, (ii) when the level of Actin A in a sample obtained from the individual is increased relative to the level of Actin A in a control sample, and (iii) when the level of P-selectin in a sample obtained from the individual is increased relative to the level of P-selectin in a control sample.

2. The method according to claim 1, wherein sample is collected within first trimester.

* * * * *